United States Patent
Yamashita et al.

(10) Patent No.: US 8,292,818 B2
(45) Date of Patent: Oct. 23, 2012

(54) ACOUSTIC LENS COMPOSITION, ULTRASONIC PROBE, AND ULTRASONIC DIAGNOSTIC APPARATUS

(75) Inventors: Yohachi Yamashita, Yokohama (JP);
Yasuharu Hosono, Yokohama (JP);
Hiroyuki Shikata, Nasu-gun (JP);
Takashi Takeuchi, Otawara (JP);
Yasuhisa Makita, Nasu-gun (JP)

(73) Assignee: Kabushiki Kaisha Toshiba, Tokyo (JP)

(*) Notice: Subject to any disclaimer, the term of this patent is extended or adjusted under 35 U.S.C. 154(b) by 476 days.

(21) Appl. No.: 12/269,568

(22) Filed: Nov. 12, 2008

(65) Prior Publication Data

US 2009/0069486 A1    Mar. 12, 2009

Related U.S. Application Data

(63) Continuation of application No. 10/902,816, filed on Aug. 2, 2004, now abandoned.

(30) Foreign Application Priority Data

Sep. 29, 2003 (JP) .................................. 2003-338564
Jun. 24, 2004 (JP) .................................. 2004-186427

(51) Int. Cl.
*A61B 8/14* (2006.01)

(52) U.S. Cl. .......... 600/472; 600/459; 73/642; 310/335; 367/150

(58) Field of Classification Search .................. 600/459, 600/472, 437; 73/642; 310/335; 367/150
See application file for complete search history.

(56) References Cited

U.S. PATENT DOCUMENTS

| | | |
|---|---|---|
| 3,944,732 A | 3/1976 | Kino |
| 4,692,653 A | 9/1987 | Kushida et al. |
| 4,901,729 A | 2/1990 | Saitoh et al. |
| 5,038,068 A | 8/1991 | Kushida et al. |
| 5,295,487 A | 3/1994 | Saitoh et al. |
| 5,410,209 A | 4/1995 | Yamashita et al. |
| 5,505,205 A | 4/1996 | Solomon et al. |
| 5,644,085 A | 7/1997 | Lorraine et al. |
| 5,921,933 A | 7/1999 | Sarkis et al. |
| 5,942,571 A | 8/1999 | Nakamura et al. |
| 5,974,884 A | 11/1999 | Sano et al. |
| 6,020,675 A | 2/2000 | Yamashita et al. |
| 6,418,084 B2 * | 7/2002 | Saito et al. ................ 367/152 |
| 6,511,739 B2 | 1/2003 | Kasai et al. |
| 6,607,491 B2 | 8/2003 | Sato |
| 6,890,644 B2 | 5/2005 | Kayanoki |
| 6,917,400 B2 * | 7/2005 | Nakamura et al. .............. 349/96 |
| 7,022,088 B2 | 4/2006 | Keast et al. |
| 7,046,439 B2 | 5/2006 | Kaminsky et al. |

(Continued)

FOREIGN PATENT DOCUMENTS

JP    53-19869    6/1978

(Continued)

OTHER PUBLICATIONS

Office Action issued Mar. 8, 2011 in Japanese Application No. 2008-251330 filed (w/English translation).

*Primary Examiner* — Brian Casler
*Assistant Examiner* — Amanda Lauritzen
(74) *Attorney, Agent, or Firm* — Oblon, Spivak, McClelland, Maier & Neustadt, L.L.P.

(57) ABSTRACT

Provided is an acoustic lens composition which comprises 40 wt % or more of silicone rubber and 15 to 60 wt % of a zinc oxide powder, suppresses ultrasonic attenuation, and has superior molding properties.

5 Claims, 2 Drawing Sheets

U.S. PATENT DOCUMENTS

| | | |
|---|---|---|
| 7,432,638 B2 | 10/2008 | Yamashita et al. |
| 2003/0202137 A1 | 10/2003 | Nakamura et al. |
| 2004/0233526 A1 | 11/2004 | Kaminsky et al. |
| 2005/0068628 A1 | 3/2005 | Masaki |
| 2005/0107783 A1 | 5/2005 | Tom et al. |
| 2005/0182326 A1* | 8/2005 | Vilkomerson ................ 600/439 |
| 2006/0079785 A1 | 4/2006 | Hosono et al. |
| 2007/0032366 A1 | 2/2007 | Kasuga et al. |
| 2007/0146887 A1 | 6/2007 | Ikeda et al. |
| 2007/0153385 A1 | 7/2007 | Sakai et al. |
| 2007/0161903 A1 | 7/2007 | Yamashita et al. |
| 2007/0167803 A1* | 7/2007 | Kaminski et al. ............ 600/459 |
| 2007/0190314 A1* | 8/2007 | Aiki et al. |
| 2007/0195431 A1 | 8/2007 | Asakura et al. |
| 2007/0197914 A1 | 8/2007 | Kosaku |
| 2007/0282204 A1 | 12/2007 | Yamashita et al. |
| 2009/0209864 A1* | 8/2009 | Yamashita et al. ........... 600/459 |
| 2009/0243436 A1* | 10/2009 | Rubinsztajn et al. ........ 310/335 |

FOREIGN PATENT DOCUMENTS

| | | |
|---|---|---|
| JP | 58-216294 | 12/1983 |
| JP | 59-190208 | 12/1984 |
| JP | 62-11897 | 1/1987 |
| JP | 62-40495 | 2/1987 |
| JP | 63-220847 | 9/1988 |
| JP | 1-34396 | 7/1989 |
| JP | 5-9039 | 2/1993 |
| JP | 8-615 | 1/1996 |
| JP | 08-020725 | 1/1996 |
| JP | 11-252695 | 9/1999 |
| JP | 2000-125395 | 4/2000 |
| JP | 2000-261891 | 9/2000 |
| JP | 2002-95081 | 3/2002 |
| JP | 2002-112999 | 4/2002 |
| JP | 2003-88522 | 3/2003 |
| JP | 2003-095655 | 4/2003 |

* cited by examiner

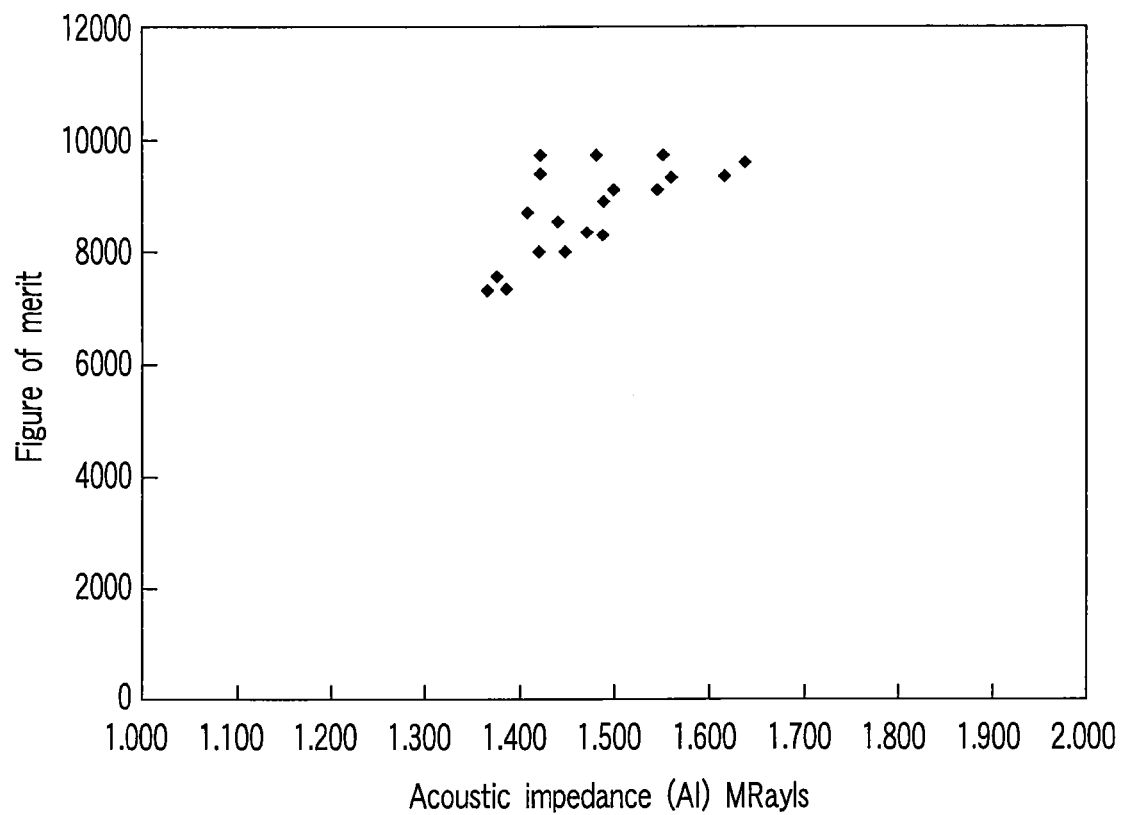
F I G. 3
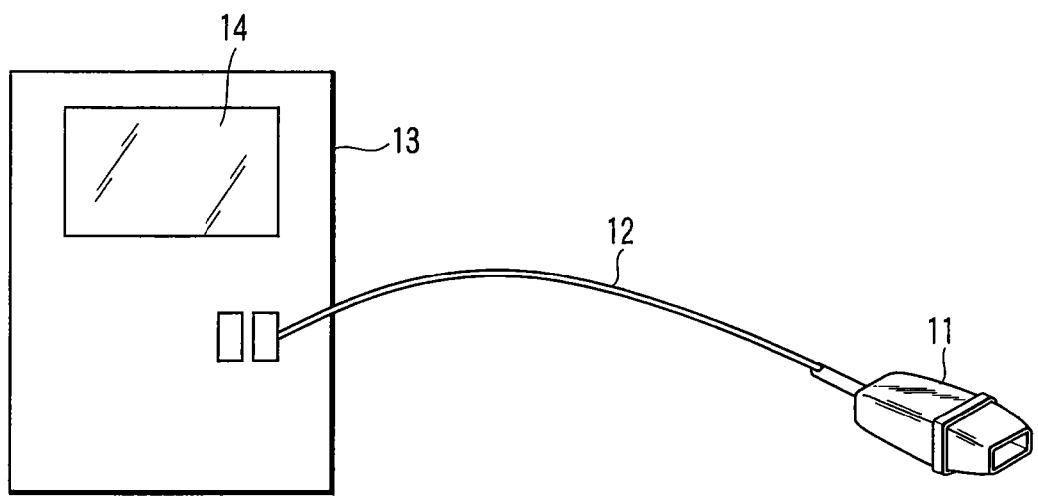
F I G. 4

ACOUSTIC LENS COMPOSITION, ULTRASONIC PROBE, AND ULTRASONIC DIAGNOSTIC APPARATUS

CROSS-REFERENCE TO RELATED APPLICATIONS

This application is a continuation of and claims the benefit of priority under 35 U.S.C. §120 from U.S. application Ser. No. 10/902,816, filed on Aug. 2, 2004, and claims the benefit of priority under 35 U.S.C §119 from Japanese Patent Applications No. 2003-338564, filed Sep. 29, 2003; and No. 2004-186427, filed Jun. 24, 2004, the entire contents of each of which are incorporated herein by reference.

BACKGROUND OF THE INVENTION

1. Field of the Invention

The present invention relates to an acoustic lens composition, ultrasonic probe and ultrasonic diagnostic apparatus.

2. Description of the Related Art

Ultrasonic probes are used in, e.g., fish detectors and ultrasonic diagnostic apparatuses for diagnosing living bodies. These ultrasonic probes use an acoustic lens to increase the resolution by focusing an ultrasonic beam.

In particular, an acoustic lens incorporated into an ultrasonic probe of an ultrasonic diagnostic apparatus for diagnosing a living body, i.e., a medical diagnostic apparatus, is desired to have a convex shape in order to improve the adhesion to a living body. In addition, this acoustic lens is desired to mainly satisfy the following six characteristics.

(1) The acoustic lens desirably minimizes the reflection of an ultrasonic wave from a living body. For this purpose, the acoustic lens is preferably made of a material by which the acoustic impedance (AI=sound velocity×density) of the lens is close to 1.53 MRayls which is the acoustic impedance of a living body.

(2) The acoustic lens desirably transmits and receives an ultrasonic wave at high speed. Therefore, the acoustic lens is preferably made of a material which decreases the attenuation ratio at the use frequency.

(3) To obtain a convex shape, the acoustic lens is desirably made of a material by which the sound velocity in the lens is lower than that (about 1,500 m/s) in a living body. In particular, the radius of curvature of the acoustic lens is calculated from the relationship between the sound velocity in the lens and that in a living body. This radius of curvature of the acoustic lens can be increased by the use of a material which makes the sound velocity of the lens lower than that in a living body. Consequently, the thickness of the acoustic lens can be decreased.

(4) The acoustic lens is desirably made of a material having good molding properties, particularly, high tear strength. That is, an acoustic lens used in an ultrasonic probe having a central frequency of about 2 to 13 MHz has a thickness of about 0.5 to 1.5 mm. To mold this acoustic lens into a highly precise convex shape, a rubber-based material desirably has high flowability. Especially in an ultrasonic probe whose central frequency exceeds 7 MHz, it is desirable to use a rubber-based material having good molding properties in order to decrease the thickness of an acoustic lens to 1.0 mm or less. Furthermore, acoustic lenses having complicated shapes such as a cap shape are recently often used, so a rubber-based material having not only good molding properties but also high tear strength is desired.

(5) The constituent material, containing additives, of the acoustic lens is desirably harmless to a living body. Also, the acoustic lens is desirably made of a material which is chemically and physically stable in an aqueous glycerin solution, ethyl alcohol, olive oil, or castor oil which is generally used as an acoustic coupling gel or disinfectant.

(6) When in use, the acoustic lens is pushed against a living body with a considerable pressure. If the rubber hardness of the acoustic lens is insufficient, the acoustic lens deforms to shift the focal point, and the image quality degrades. Accordingly, the acoustic lens is desirably made of a material having a durometer A hardness of 50° or more.

The attenuation characteristics of the acoustic lens largely depend not only on the attenuation ratio described in (2) but also on the product of the attenuation ratio and sound velocity. Therefore, the acoustic lens is preferably made of a material which is advantageous in FOM (Figure of Merit). The value of FOM is favorably as low as possible for the same acoustic impedance.

The conventional acoustic lens is made of a rubber-based material obtained by mixing a silica powder in silicone rubber.

Also, Jpn. Pat. Appln. KOKOKU Publication No. 1-34396 discloses an acoustic lens obtained by mixing a predetermined amount of a titanium oxide powder having a predetermined particle diameter in natural silicone rubber.

Jpn. Pat. Appln. KOKOKU Publication No. 5-9039 discloses an acoustic lens composition made up of a silicone rubber compound, an aluminum powder and titanium oxide powder having predetermined particle diameters, and a thermoplastic resin such as nylon having a melting point of 80° C. or more.

Jpn. Pat. Appln. KOKAI Publication No. 8-615 discloses an acoustic lens obtained by adding zinc oxide as a vulcanization assistant to a mixture of silicone-based rubber and butadiene rubber.

In an acoustic lens having a composition obtained by adding a silica powder to silicone rubber, however, the addition amount of the silica powder must be increased to make the acoustic impedance approach 1.53 MRayls which is the acoustic impedance of a living body. The density of a silica powder is about 2.2 g/cm$^3$. To set the density of the whole acoustic lens at about 1.4 to 1.6 g/cm$^3$, therefore, a fine silica powder having an average particle diameter of about 15 to 30 nm, i.e., having a large specific area must be so mixed as to have a weight of about 40 to 50 wt % and a volume of about 24 to 32 vol %. This not only makes incorporation of this amount of the silica powder into silicone rubber difficult, but also makes deaeration after the incorporation difficult. In addition, since the flowability of silicone rubber lowers during molding of the acoustic lens, cracks and pores easily form. The tear strength of the acoustic lens also lowers. On the other hand, although the ratio of attenuation to silicone rubber caused by the addition of this silica powder is relatively low, the sound velocity described in (3) is about 1,000 m/s or more. Consequently, even if the attenuation ratio of the acoustic lens is low, the thickness cannot be decreased. This lowers the value of FOM (attenuation ratio×sound velocity) described above, and increases attenuation.

In the acoustic lenses described in Jpn. Pat. Appln. KOKOKU Publication Nos. 1-34396 and 5-9039, the added titanium oxide powder and alumina powder have the effect of decreasing the sound velocity, when compared to the silica powder. However, to make the acoustic impedances of these acoustic lenses approach 1.53 MRayls as the acoustic impedance of a living body, the addition amounts of titanium oxide and alumina with respect to silicone rubber must be increased as in the case of the silica powder. As a consequence, these acoustic lenses not only increase the attenuation ratio described in (2), but also deteriorate the molding properties described in (4).

Furthermore, the acoustic lens described in Jpn. Pat. Appln. KOKAI Publication No. 8-615 contains a mixture of silicone-based rubber and butadiene-based rubber. This causes swell upon use of olive oil or castor oil as an acoustic coupling material, and lowers the long-term reliability.

BRIEF SUMMARY OF THE INVENTION

According to a first aspect of the present invention, there is provided an acoustic lens composition comprising 40 wt % or more of silicone rubber and 15 to 60 wt % of a zinc oxide powder.

According to a second aspect of the present invention, there is provided an acoustic lens composition comprising 40 wt % or more of silicone rubber and 10 to 52 wt % of at least one platinum-based powder selected from the group consisting of a platinum powder, a platinum powder having platinum oxide on at least a surface, and a platinum oxide powder.

According to a third aspect of the present invention, there is provided an acoustic lens composition comprising 40 wt % or more of silicone rubber and 12 to 56 wt % of a ytterbium oxide powder.

According to a fourth aspect of the present invention, there is provided an ultrasonic probe comprising:
a backing material;
a piezoelectric element formed on the backing material, and having a piezoelectric body and a pair of electrodes formed on a first surface of the piezoelectric body, which faces the backing material, and on a second surface of the piezoelectric body, which is opposite to the first surface;
an acoustic matching layer formed on the electrode surface of the piezoelectric element; and
an acoustic lens formed on the acoustic matching layer, and containing 40 wt % or more of silicone rubber and 15 to 60 wt % of a zinc oxide powder.

According to a fifth aspect of the present invention, there is provided an ultrasonic probe comprising:
a backing material;
a piezoelectric element formed on the backing material, and having a piezoelectric body and a pair of electrodes formed on a first surface of the piezoelectric body, which faces the backing material, and on a second surface of the piezoelectric body, which is opposite to the first surface;
an acoustic matching layer formed on the electrode surface of the piezoelectric element; and
an acoustic lens formed on the acoustic matching layer, and containing 40 wt % or more of silicone rubber and 10 to 52 wt % of at least one platinum-based powder selected from the group consisting of a platinum powder, a platinum powder having platinum oxide on at least a surface, and a platinum oxide powder.

According to a sixth aspect of the present invention, there is provided an ultrasonic probe comprising:
a backing material;
a piezoelectric element formed on the backing material, and having a piezoelectric body and a pair of electrodes formed on a first surface of the piezoelectric body, which faces the backing material, and on a second surface of the piezoelectric body, which is opposite to the first surface;
an acoustic matching layer formed on the electrode surface of the piezoelectric element; and
an acoustic lens formed on the acoustic matching layer, and containing 40 wt % or more of silicone rubber and 12 to 56 wt % of a ytterbium oxide powder.

According to a seventh aspect of the present invention, there is provided an ultrasonic diagnostic apparatus comprising:
an ultrasonic probe having an acoustic lens formed on a piezoelectric element via an acoustic matching layer, and containing 40 wt % or more of silicone rubber and 15 to 60 wt % of a zinc oxide powder;
an ultrasonic diagnostic apparatus main body having a screen; and
a cable which connects the ultrasonic probe and the ultrasonic diagnostic apparatus main body.

According to an eighth aspect of the present invention, there is provided an ultrasonic diagnostic apparatus comprising:
an ultrasonic probe having an acoustic lens formed on a piezoelectric element via an acoustic matching layer, and containing 40 wt % or more of silicone rubber and 10 to 52 wt % of at least one platinum-based powder selected from the group consisting of a platinum powder, a platinum powder having platinum oxide on at least a surface, and a platinum oxide powder;
an ultrasonic diagnostic apparatus main body having a screen; and
a cable which connects the ultrasonic probe and the ultrasonic diagnostic apparatus main body.

According to a ninth aspect of the present invention, there is provided an ultrasonic diagnostic apparatus comprising:
an ultrasonic probe having an acoustic lens formed on a piezoelectric element via an acoustic matching layer, and containing 40 wt % or more of silicone rubber and 12 to 56 wt % of a ytterbium oxide powder;
an ultrasonic diagnostic apparatus main body having a screen; and
a cable which connects the ultrasonic probe and the ultrasonic diagnostic apparatus main body.

BRIEF DESCRIPTION OF THE SEVERAL VIEWS OF THE DRAWING

FIG. 3 is a graph showing the relationship between the acoustic impedance and FOM of each of acoustic lenses according to Examples 1 to 23 of the present invention; and FIG. 4 is a schematic view of an ultrasonic diagnostic apparatus according to an embodiment of the present invention.

DETAILED DESCRIPTION OF THE INVENTION

Figure 1:
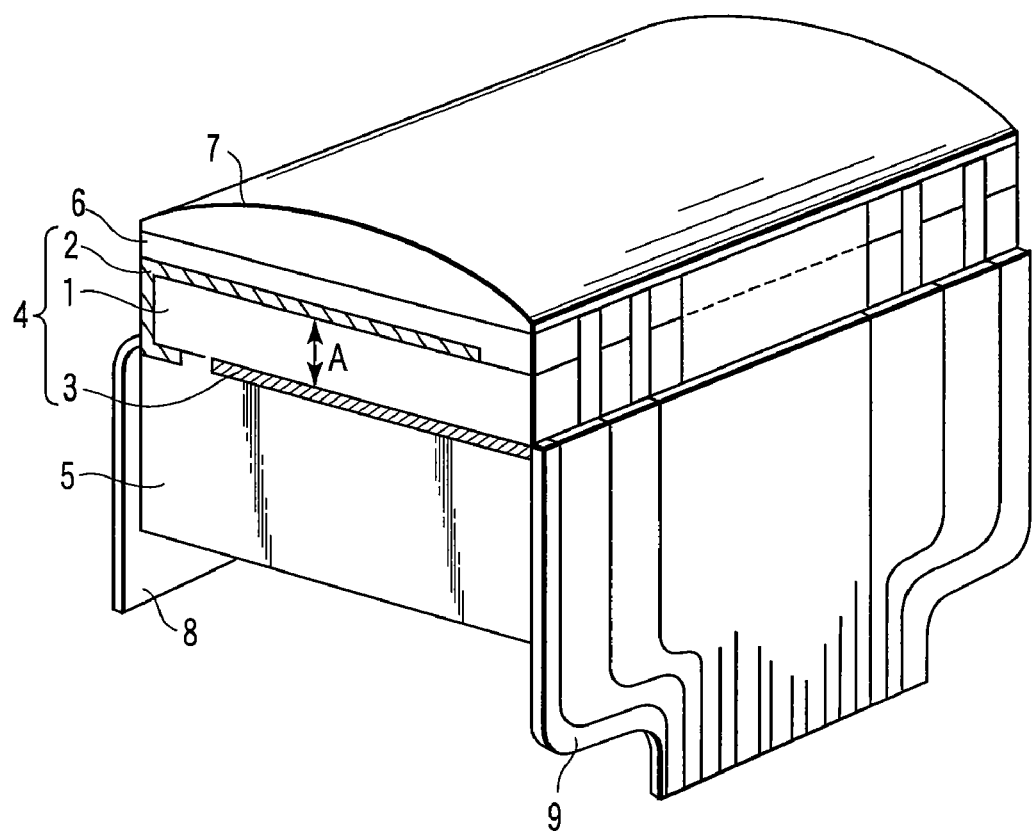
FIG. 1 is a perspective view of an ultrasonic probe according to an embodiment of the present invention.

Embodiments of the present invention will be described in detail below.
(First Embodiment)

An acoustic lens composition according to the first embodiment comprises 40 wt % or more of silicone rubber and 15 to 60 wt % of zinc oxide (ZnO).

The silicone rubber is a material having a siloxane bond, which is an Si—O bond, as a molecular skeleton. For example, as the silicone rubber, a material containing dimethylpolysiloxane as a main component, or the like can be used. The silicone rubber is roughly classified into liquid silicone rubber having a polymerization degree of 100 to 2,000, and millable silicone rubber having a polymerization degree of 3,000 to 10,000.

The content of the silicone rubber in the acoustic lens composition is 40 wt % or more. If the silicone rubber content is less than 40 wt %, not only the molding properties may deteriorate, but also the attenuation ratio of an ultrasonic wave may increase. In an acoustic lens having the composition, it may also become impossible to obtain a necessary sound velocity or acoustic impedance. The content of the silicone rubber in the acoustic lens composition is more preferably 50 wt % or more.

The content of the zinc oxide powder in the acoustic lens composition is 15 to 60 wt %. If the content of the zinc oxide powder is less than 15 wt %, it may become difficult to well achieve the effect of lowering the sound velocity of an acoustic lens having the composition, and no appropriate FOM may be obtained. Also, since the density cannot be well increased, it is difficult to set the acoustic lens at a necessary acoustic impedance of about 1.3 to 1.7 MRayls. If the content of the zinc oxide powder exceeds 60 wt %, not only the acoustic impedance of the acoustic lens may increase too much, but also the attenuation ratio of an ultrasonic wave may increase. Furthermore, if the content of the zinc oxide powder falls outside the above range, an acoustic lens having an appropriate rubber hardness is difficult to obtain. The content of the zinc oxide powder in the acoustic lens composition is more preferably 20 to 55 wt %, and most preferably, 30 to 55 wt %.

The zinc oxide powder preferably has an average particle diameter of 200 nm or less. Since a fine zinc oxide powder like this can be evenly dispersed in silicone rubber, it is possible to further suppress attenuation of an ultrasonic wave, and further improve the molding properties. The average particle size of the zinc oxide powder is more preferably 1 to 100 nm, and most preferably, 10 to 50 nm. Note that the average particle size can be calculated by using the value of the specific surface area ($m^2/g$) of a powder to be measured by assuming that each particle is spherical.

The surface of the zinc oxide powder permits to be coated with a silicone resin. As this silicone resin, methicone, dimethicone, or the like can be used. The silicone-resin-coated zinc oxide powder can be obtained by, e.g., dipping a zinc oxide powder in a solution of the silicone resin, extracting the zinc oxide powder from the solution, and drying the extracted powder. The thus obtained silicone-resin-coated zinc oxide powder can be easily incorporated into silicone rubbers and has uniform dispersibility. Therefore, it is possible to further suppress attenuation of an ultrasonic wave and further improve the molding properties. The coating amount of the silicone resin is preferably 1 to 10 wt % with respect to the zinc oxide powder.

The acoustic lens composition according to the first embodiment of the present invention contains a vulcanizing agent. For example, a peroxide-based vulcanizing agent, such as 2,5-dimethyl-2,5-ditertiarybutylperoxyhexane, p-methylbenzoylperoxide, or ditertiarybutylperoxide is used. The amount of the peroxide-based vulcanizing agent is preferably about 0.3 to 2 wt % with respect to the silicone rubber in the acoustic lens composition. It is also possible to use a vulcanizing agent other than the peroxide-based vulcanizing agent.

The acoustic lens composition according to the first embodiment of the present invention permits to contain 30 wt % or less of a silica ($SiO_2$) powder. This silica powder has a function of increasing the strength of an acoustic lens having the composition. If the content of the silicon powder in the acoustic lens composition exceeds 30 wt %, attenuation of an ultrasonic wave appears, while the molding properties deteriorate. This makes molding of a precise acoustic lens difficult. The content of the silica powder in the acoustic lens composition is more preferably 20 wt % or less.

The average particle diameter of the silica powder is preferably 50 nm or less, and more preferably, 20 nm or less. A preferred example of the silica powder is aerosil silica.

The acoustic lens composition according to the first embodiment of the present invention permits to contain a small amount of additives as long as the characteristics of an acoustic lens having the composition do not deteriorate. Examples of the additives are titanium oxide, alumina, cerium oxide, iron oxide, barium oxide, an organic filler, and a coloring pigment. These additives do not largely deteriorate the effects of the embodiment of the present invention, provided that the amount of the additives in the acoustic lens composition is about 5 wt % or less.

A method of manufacturing an acoustic lens by using the acoustic lens composition according to the first embodiment will be explained below.

First, a zinc oxide powder is dried to evaporate adhered water and the like. This zinc oxide powder and, if necessary, a silica powder are added to silicone rubber, and these materials are kneaded such that the density is about 1.4 to 2.0 $g/cm^3$. A vulcanizing agent such as a peroxide-based vulcanizing agent described above are added to the kneaded product, and vulcanization molding is performed at about 100 to 180° C., thereby forming a molded product having the shape of an acoustic lens. Subsequently, this molded product undergoes secondary vulcanization at a temperature of about 180 to 240° C., thereby manufacturing an acoustic lens.

The vulcanization method using a peroxide under the above conditions makes it possible to obtain an acoustic lens having sufficient strength and low attenuation. By appropriately selecting the silicone rubber and vulcanizing agent, the temperature or time of secondary vulcanization can be lowered or reduced, or secondary vulcanization can be omitted.

An ultrasonic probe using the acoustic lens having the above composition will be described below with reference to the accompanying drawing.

FIG. 1 is a perspective view of an ultrasonic probe when piezoelectric elements and acoustic matching layers are arranged into the form of a one-dimensional array. A piezoelectric element 4 including a piezoelectric body 1 and first and second electrodes 2 and 3 is adhered to a backing material 5. An acoustic matching layer 6 is formed on an ultrasonic transmitting/receiving surface of the piezoelectric element 4. The piezoelectric body 1 is divided into a plurality of portions together with the first and second electrodes 2 and 3 and acoustic matching layer 6. Each divided piezoelectric body 1 assumes a strip shape, and has an ultrasonic transmitting/receiving surface which is a surface having the second largest area. Each piezoelectric body 1 vibrates in the direction of an arrow A in FIG. 1. Each first electrode 2 is formed over the ultrasonic transmitting/receiving surface, one side surface, and a portion of a surface opposite to the ultrasonic transmitting/receiving surface of the piezoelectric body 1. Each second electrode 3 is formed on the surface opposite to the ultrasonic transmitting/receiving surface of the piezoelectric body 1 with a predetermined distance from the first electrode 2 so as to be insulated from it.

An acoustic lens 7 is formed on the acoustic matching layers 6. Each line of a ground electrode plate 8 is connected to each first electrode 2. Each line of a flexible printed circuit board 9 is connected to each second electrode 3 by, e.g., soldering.

The operation of this ultrasonic probe having the above arrangement will be explained below. An ultrasonic wave is transmitted from the ultrasonic transmitting receiving surface by resonating the piezoelectric body 1 by applying a voltage between the first and second electrodes 2 and 3. In reception, the piezoelectric body 1 is vibrated by an ultrasonic wave received from the ultrasonic transmitting/receiving surface, and this vibration is electrically converted into a signal, thereby obtaining an image.

An ultrasonic diagnostic apparatus including the above ultrasonic probe will be described below with reference to FIG. 4. A medical ultrasonic diagnostic apparatus (or an ultrasonic image inspecting apparatus) which forms an image of an object to be diagnosed by transmitting an ultrasonic wave to the object and receiving a reflection signal (echo signal) from the object has an array type ultrasonic probe 11 having an ultrasonic signal transmitting/receiving function. An acoustic lens having the composition described previously is incorporated into the ultrasonic probe 11. The ultrasonic probe 11 is connected to an ultrasonic diagnostic apparatus main body 13 via a cable 12. The ultrasonic diagnostic apparatus main body 13 has a screen 14.

In the first embodiment described above, an acoustic lens composition comprises 40 wt % or more of silicone rubber and 15 to 60 wt % of a zinc oxide powder. Accordingly, when the acoustic lens composition is molded into a complicated cap-like lens shape, good molding properties is not only represented, but also an acoustic lens having high tear strength is obtained. At the same time, it is possible to obtain an acoustic lens having an acoustic impedance close to that of a living body, a low attenuation ratio, a sound velocity lower than the sound velocity (about 1,500 m/s) in a living body, and a small FOM value which is the product of the attenuation ratio and sound velocity.

That is, when the acoustic lens composition is molded, the density of the zinc oxide is as high as about 5.6 g/cm$^3$, so this zinc oxide power can be incorporated into silicone rubber with a volume ratio lower than a weight ratio. As a consequence, the zinc oxide powder can be easily incorporated into silicone rubber. This makes it possible to improve the molding properties, and obtain an acoustic lens having high mechanical strength, such as tear strength, resulting from uniform dispersion. Especially when a zinc oxide powder having an average particle diameter of 200 nm or less is used, the properties of incorporation into silicone rubber can be improved. Also, the use of a zinc oxide powder whose surface is coated with a silicone resin can further improve the properties of incorporation into silicone rubber. Furthermore, when 30 wt % or less of a silica powder comprise in the silicone rubber and zinc oxide powder, the mechanical strength such as the tear strength of the acoustic lens can be further increased.

Since 15 to 60 wt % of a zinc oxide powder having a high density are contained in silicone rubber, it is possible to obtain an acoustic lens having an acoustic impedance of, e.g., about 1.3 to 1.7 Mrayls which is close to that of a living body, a low attenuation ratio of an ultrasonic wave (e.g., about 12 dB/mm or less) at a frequency of about 10 MHz, a sound velocity of, e.g., about 820 to 980 m/s which is lower than the sound velocity (about 1,500 m/s) in a living body, and a small FOM value of, e.g., 10,000 or less.

Especially when added within the above range, a zinc oxide powder achieves the effect of suppressing attenuation of an ultrasonic wave, e.g., the effect of decreasing the attenuation ratio to about 12 dB/mm or less at a frequency of about 10 MHz. The present inventors studied the ultrasonic attenuating effects of $ZrO_2$, $Fe_2O_3$, and $BaSO_4$ powders which can be contained in silicone rubber and have densities equivalent to that of zinc oxide. Consequently, the present inventors have found that the powders of these compounds have a very small effect of suppressing attenuation of an ultrasonic wave, and zinc oxide uniquely functions to suppress attenuation of an ultrasonic wave.

It is also possible to obtain an acoustic lens having a density of about 1.4 to 2.0 g/cm$^3$ which is suited to setting the value of the acoustic impedance at about 1.3 to 1.7 Mrayls.

Furthermore, the base material of the acoustic lens having the composition according to the first embodiment is silicone rubber. This imparts the acoustic lens stable chemical and physical properties with respect to an aqueous glycerin solution, ethyl alcohol, olive oil, or castor oil which is generally used as an acoustic coupling gel or disinfectant. Additionally, the acoustic lens has a durometer A hardness of 50° or more because the lens contains a predetermined amount of a zinc oxide powder.

Also, when 30 wt % or less of a silica powder are contained in the silicone rubber and zinc oxide powder, the mechanical strength such as the tear strength of the acoustic lens can be further increased.

This decreases the thickness, increases the ultrasonic transmitting/receiving sensitivity, and reduces deterioration of the frequency characteristics of the acoustic lens of the first embodiment.

It is also possible to increase the resolution and sensitivity of ultrasonic images of an ultrasonic probe incorporating the acoustic lens having the above characteristics.

(Second Embodiment)

An acoustic lens composition according to the second embodiment comprises 40 wt % or more of silicone rubber, and 10 to 52 wt % of at least one platinum-based powder selected from a platinum powder, a platinum powder having platinum oxide on at least the surface, and a platinum oxide powder.

The silicone rubber is the same as that explained in the first embodiment and also has the same functions as in the first embodiment.

The content of the platinum-based powder in the acoustic lens composition is 10 to 52 wt %. If the content of the platinum-based powder is less than 10 wt %, it may become difficult to well achieve the effect of lowering the sound velocity of an acoustic lens having the composition, and no appropriate FOM may be obtained. Also, since the density cannot be well increased, it is difficult to set the acoustic lens at a necessary acoustic impedance of about 1.3 to 1.7 MRayls. If the content of the platinum-based powder exceeds 52 wt %, not only the acoustic impedance of the acoustic lens may increase too much, but also the attenuation ratio of an ultrasonic wave may increase. Furthermore, if the content of the platinum-based powder falls outside the above range, an acoustic lens having an appropriate rubber hardness is difficult to obtain. The content of the platinum-based powder in the acoustic lens composition is more preferably 15 to 47 wt %, and most preferably, 25 to 47 wt %.

The platinum-based powder preferably has an average particle diameter of 200 nm or less. Since a fine platinum-based powder like this can be evenly dispersed in silicone rubber, it is possible to further suppress attenuation of an ultrasonic wave, and further improve the molding properties. The average particle size of the platinum-based powder is more preferably 1 to 100 nm, and most preferably, 10 to 50 nm. Especially when the lower limit of the powder is limited to 10 nm, it is possible to prevent spontaneous combustion, and perform safe operations.

The surface of the platinum-based powder can be coated with a silicone resin. As this silicone resin, methicone, dimethicone, or the like can be used. The silicone-resin-coated powder can be obtained by, e.g., dipping a platinum-based powder in a solution of the silicone resin, extracting the powder from the solution, and drying the extracted powder. The thus obtained silicone-resin-coated powder can be easily incorporated into silicone rubber, and has uniform dispersibility. Therefore, it is possible to further suppress attenuation of an ultrasonic wave and further improve the molding properties. The coating amount of the silicone resin is preferably 1 to 10 wt % with respect to the platinum-based powder.

The acoustic lens composition according to the second embodiment of the present invention contains a vulcanizing agent. For example, a peroxide-based vulcanizing agent, such as 2,5-dimethyl-2,5-ditertiarybutylperoxyhexane, p-methylbenzoylperoxide, or ditertiarybutylperoxide is used. The amount of the peroxide-based vulcanizing agent is preferably about 0.3 to 2 wt % with respect to the silicone rubber in the acoustic lens composition. It is also possible to use a vulcanizing agent other than the peroxide-based vulcanizing agent.

As explained in the first embodiment, the acoustic lens composition according to the second embodiment of the present invention permits to contain 30 wt % or less of a silica powder. The content of the silica powder in the acoustic lens composition is more preferably 20 wt % or less.

The average particle diameter of the silica powder is preferably 50 nm or less, and more preferably, 20 nm or less. A preferred example of the silica powder is aerosil silica.

The acoustic lens composition according to the second embodiment of the present invention permits to contain a small amount of additives as long as the characteristics of the acoustic lens do not deteriorate. Examples of the additives are titanium oxide, alumina, cerium oxide, iron oxide, barium oxide, an organic filler, and a coloring pigment. These additives do not largely deteriorate the effect of the embodiment of the present invention, provided that the amount of the additives in the acoustic lens composition is about 5 wt % or less.

An acoustic lens is manufactured from the acoustic lens composition according to the second embodiment by the same method as in the first embodiment described earlier except that at least one platinum-based powder selected from a platinum powder, a platinum powder having platinum oxide on at least the surface, and a platinum oxide powder is used instead of a zinc oxide powder.

An ultrasonic probe and ultrasonic diagnostic apparatus using the acoustic lens having the above composition have the same structures as explained in FIGS. 1 and 4 and the first embodiment.

In the second embodiment described above, an acoustic lens composition comprises 40 wt % or more of silicone rubber and 10 to 52 wt % of at least one platinum-based powder selected from a platinum powder, a platinum powder having platinum oxide on at least the surface, and a platinum oxide powder. Accordingly, as in the first embodiment, when the acoustic lens composition is molded into a complicated cap-like lens shape, good molding properties is not only represented, but also an acoustic lens having high tear strength is obtained. At the same time, it is possible to obtain an acoustic lens having superior characteristics, i.e., an acoustic impedance of, e.g., about 1.3 to 1.7 Mrayls which is close to that of a living body, a low attenuation ratio (e.g., about 12 dB/mm or less) at a frequency of about 10 MHz, a sound velocity of, e.g., about 820 to 980 m/s which is lower than the sound velocity (about 1,500 m/s) in a living body, and a small FOM value, which is the product of the attenuation ratio and sound velocity, of 10,000 or less, and also having a density of about 1.4 to 2.0 g/cm$^3$ which is suited to setting the above-mentioned value of the acoustic impedance.

Especially when added within the above range, a platinum-based powder, e.g., a platinum powder having a high density of about 21 g/cm$^3$ can set the acoustic impedance at, e.g., about 1.3 to 1.7 Mrayls which is close to that of a living body, and also achieves the effect of suppressing attenuation of an ultrasonic wave. The present inventors studied the ultrasonic attenuating effects of gold and tungsten powders which can be contained in silicone rubber and have densities equivalent to that of platinum. Consequently, the present inventors have found that the powders of these compounds have a very small effect of suppressing attenuation of an ultrasonic wave, and a platinum powder (including a platinum powder having an oxidized surface, or the like) uniquely functions to suppress attenuation of an ultrasonic wave.

Also, when 30 wt % or less of a silica powder are contained in the silicone rubber and platinum-based powder, the mechanical strength such as the tear strength of the acoustic lens can be further increased.

Accordingly, when the acoustic lens composition of the second embodiment is used, it is possible to obtain an acoustic lens having a small thickness, increased ultrasonic transmitting/receiving sensitivity, and reduced deterioration of the frequency characteristics.

It is also possible to increase the resolution and sensitivity of ultrasonic images of an ultrasonic probe incorporating the acoustic lens having the above characteristics.

(Third Embodiment)

An acoustic lens composition according to the third embodiment comprises 40 wt % or more of silicone rubber, and 12 to 56 wt % of a ytterbium oxide ($Yb_2O_3$) powder.

The silicone rubber is the same as that explained in the first embodiment and also has the same functions as in the first embodiment.

The content of the ytterbium oxide powder in the acoustic lens composition is 12 to 56 wt %. If the content of the ytterbium oxide powder is less than 12 wt %, it may become difficult to well achieve the effect of lowering the sound velocity of an acoustic lens having the composition, and no appropriate FOM may be obtained. Also, since the density cannot be well increased, it is difficult to set the acoustic lens at a necessary acoustic impedance of about 1.3 to 1.7 MRayls. If the content of the ytterbium oxide powder exceeds 56 wt %, not only the acoustic impedance of the acoustic lens may increase too much, but also the attenuation ratio of an ultrasonic wave may increase. Furthermore, if the content of the ytterbium oxide powder falls outside the above range, an acoustic lens having an appropriate rubber hardness is difficult to obtain. The content of the ytterbium oxide powder in the acoustic lens composition is more preferably 17 to 51 wt %, and most preferably, 27 to 51 wt %.

The ytterbium oxide powder preferably has an average particle diameter of 200 nm or less. Since a fine ytterbium oxide powder like this can be evenly dispersed in silicone rubber, it is possible to further suppress attenuation of an ultrasonic wave, and further improve the molding properties. The average particle size of the ytterbium oxide powder is more preferably 1 to 100 nm, and most preferably, 10 to 50 nm.

The surface of the ytterbium oxide powder can be coated with a silicone resin. As this silicone resin, methicone, dimethicone, or the like can be used. The silicone-resin-coated powder can be obtained by, e.g., dipping a ytterbium oxide powder in a solution of the silicone resin, extracting the powder from the solution, and drying the extracted powder. The thus obtained silicone-resin-coated powder can be easily incorporated into silicone rubber, and has uniform dispersibility. Therefore, it is possible to further suppress attenuation of an ultrasonic wave and further improve the molding properties. The coating amount of the silicone resin is preferably 1 to 10 wt % with respect to the ytterbium oxide powder.

The acoustic lens composition according to the third embodiment of the present invention contains a vulcanizing agent. For example, a peroxide-based vulcanizing agent, such as 2,5-dimethyl-2,5-ditertiarybutylperoxyhexane, p-methylbenzoylperoxide, or ditertiarybutylperoxide is used. The amount of the peroxide-based vulcanizing agent is preferably about 0.3 to 2 wt % with respect to the silicone rubber in the acoustic lens composition. It is also possible to use a vulcanizing agent other than the peroxide-based vulcanizing agent.

As explained in the first embodiment, the acoustic lens composition according to the third embodiment of the present invention permits to contain 30 wt % or less of a silica powder. The content of the silica powder is more preferably 20 wt % or less.

The average particle diameter of the silica powder is preferably 50 nm or less, and more preferably, 20 nm or less. A preferred example of the silica powder is aerosil silica.

The acoustic lens composition according to the third embodiment of the present invention permits to contain a small amount of additives as long as the characteristics of the acoustic lens do not deteriorate. Examples of the additives are titanium oxide, alumina, cerium oxide, iron oxide, barium oxide, an organic filler, and a coloring pigment. These additives do not largely deteriorate the effect of the embodiment of the present invention, provided that the amount of the additives in the acoustic lens composition is about 5 wt % or less.

An acoustic lens is manufactured from the acoustic lens composition according to the third embodiment by the same method as in the first embodiment described earlier except that a ytterbium oxide powder is used instead of a zinc oxide powder.

An ultrasonic probe and ultrasonic diagnostic apparatus using the acoustic lens having the above composition have the same structures as explained in FIGS. 1 and 4 and the first embodiment.

In the third embodiment described above, an acoustic lens composition comprises 40 wt % or more of silicone rubber and 12 to 56 wt % of a ytterbium oxide powder. Accordingly, as in the first embodiment, when the acoustic lens composition is molded into a complicated cap-like lens shape, good molding properties is not only represented, but also an acoustic lens having high tear strength is obtained. At the same time, it is possible to obtain an acoustic lens having superior characteristics, i.e., an acoustic impedance of, e.g., about 1.3 to 1.7 Mrayls which is close to that of a living body, a low attenuation ratio (e.g., 12 dB/mm or less) at a frequency of about 10 MHz, a sound velocity of, e.g., about 820 to 980 m/s which is lower than the sound velocity (about 1,500 m/s) in a living body, and a small FOM value, which is the product of the attenuation ratio and sound velocity, of 10,000 or less, and also having a density of about 1.4 to 2.0 g/cm$^3$ which is suited to setting the above-mentioned value of the acoustic impedance.

Especially when added within the above range, a ytterbium oxide powder having a high density of about 9.0 g/cm$^3$ can set the acoustic impedance at, e.g., about 1.3 to 1.7 Mrayls which is close to that of a living body, and also achieves the effect of suppressing attenuation of an ultrasonic wave. The present inventors studied the ultrasonic attenuating effects of lutetium oxide and bismuth oxide powders which can be contained in silicone rubber and have densities equivalent to that of ytterbium oxide. Consequently, the present inventors have found that the powders of these compounds have a very small effect of suppressing attenuation of an ultrasonic wave, and a ytterbium oxide powder uniquely functions to suppress attenuation of an ultrasonic wave.

Also, when 30 wt % or less of a silica powder are contained in the silicone rubber and ytterbium oxide powder, the mechanical strength such as the tear strength of the acoustic lens can be further increased.

Accordingly, when the acoustic lens composition of the third embodiment is used, it is possible to obtain an acoustic lens having a small thickness, increased ultrasonic transmitting/receiving sensitivity, and reduced deterioration of the frequency characteristics.

It is also possible to increase the resolution and sensitivity of ultrasonic images of an ultrasonic probe incorporating the acoustic lens having the above characteristics.

Note that in another embodiment of the present invention, an acoustic lens can be manufactured from an acoustic lens composition comprising silicone rubber and two or more types of powders selected from the group consisting of a zinc oxide powder, at least one powder selected from a platinum powder having platinum oxide on at least the surface and a platinum oxide powder, and a ytterbium oxide powder. In this embodiment, each powder is mixed in silicone rubber within the range described above.

The present invention will be described in more detail below by way of its examples.

EXAMPLE 1

First, a zinc oxide (ZnO) powder having an average particle diameter of 30 nm was placed in a thermostat bath at 200° C. and dried for 2 hrs to evaporate adhered water and the like.

Figure 2:
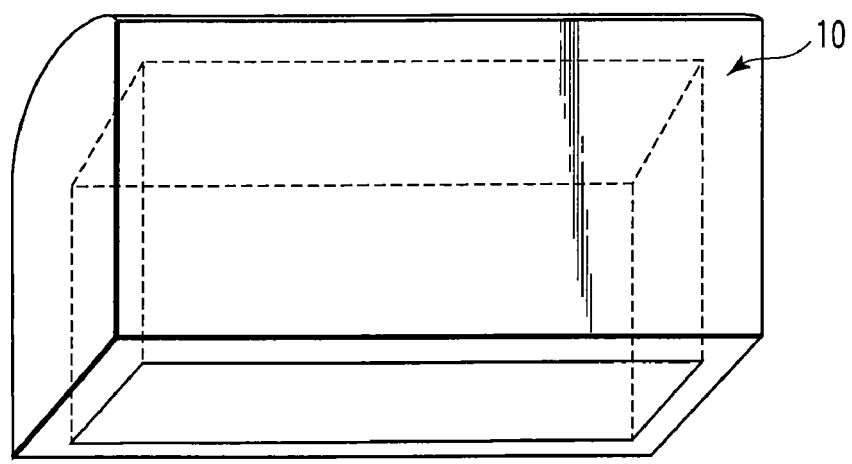
FIG. 2 is a perspective view of a cap acoustic lens according to the embodiment of the present invention.

A rubber-based composition was prepared by weighing materials such that the amount of silicone rubber as base rubber was 0.60 parts by weight and the amount of ZnO powder was 0.40 parts by weight. This rubber-based composition was well kneaded by using a two-stage roll. Subsequently, 2,5-dimethyl-2,5-ditertiarybutylperoxyhexane as a vulcanizing agent was added to the rubber-based composition such that the amount of the vulcanizing agent was 1.0 wt % with respect to the silicone rubber in the rubber-based composition, and the resultant acoustic lens composition was further kneaded. After that, the kneaded acoustic lens composition underwent vulcanization molding at a temperature of 170° C. for 15 min to form a 30×30×1 mm$^3$ square rubber plate for evaluation. In addition, the same kneaded acoustic lens composition was used to form a hollow rubber cap 10 shown in FIG. 2 under the same conditions by vulcanization molding. These vulcanized molded products underwent secondary vulcanization for 4 hrs in a dryer held at 200° C.

EXAMPLES 2-5

Vulcanized molded products (evaluation rubber plates and hollow rubber caps) having undergone secondary vulcanization were manufactured following the same procedures as in Example 1, except that four types of rubber-based compositions described below were used. A rubber-based composition used as Example 2 was prepared by silicone rubber and a ZnO powder having an average particle diameter of 30 nm which were mixed at weight ratio of 0.5:0.5. A rubber-based composition used as Example 3 was prepared by silicone rubber and a ZnO powder having an average particle diameter of 30 nm which were mixed at weight ratio of 0.45:0.55. A rubber-based composition used as Example 4 was prepared by silicone rubber, a ZnO powder having an average particle diameter of 30 nm, and a silica (SiO$_2$) powder having an average particle diameter of 16 nm which were mixed at weight ratio of 0.5:0.4:0.1. A rubber-based composition used as Example 5 was prepared by silicone rubber, a ZnO powder having an average particle diameter of 30 nm, and a silica ($SiO_2$) powder having an average particle diameter of 16 nm which were mixed at weight ratio of 0.48:0.42:0.1.

COMPARATIVE EXAMPLES 1 & 2

Vulcanized molded products (evaluation rubber plates and hollow rubber caps) having undergone secondary vulcanization were manufactured following the same procedures as in Example 1, except that two types of rubber-based compositions described below were used. A rubber-based composition used as Comparative Example 1 was prepared by silicone rubber and a ZnO powder having an average particle diameter of 30 nm which were mixed at a weight ratio of 0.9:0.1. A rubber-based composition used as Comparative Example 2 was prepared by silicone rubber and a ZnO powder having an average particle diameter of 30 nm which were mixed at a weight ratio of 0.38:0.62.

COMPARATIVE EXAMPLES 3-8

Vulcanized molded products (evaluation rubber plates and hollow rubber caps) having undergone secondary vulcanization were manufactured following the same procedures as in Example 1, except that six types of rubber-based compositions described below were used. A rubber-based composition used as Comparative Example 3 was prepared by silicone rubber and an $SiO_2$ powder having an average particle diameter of 16 nm which were mixed at a weight ratio of 0.5:0.5. A rubber-based composition used as Comparative Example 4 was prepared by silicone rubber and a titanium oxide ($TiO_2$) powder having an average particle diameter of 100 nm which were mixed at a weight ratio of 0.45:0.55. A rubber-based composition used as Comparative Example 5 was prepared by silicone rubber and an alumina ($Al_2O_3$) powder having an average particle diameter of 500 nm which were mixed at a weight ratio of 0.45:0.55. A rubber-based composition used as Comparative Example 6 was prepared by silicone rubber, butadiene rubber, and a ZnO powder having an average particle diameter of 30 nm which were mixed at a weight ratio of 0.48:0.48:0.04. A rubber-based composition used as Comparative Example 7 was prepared by silicone rubber and a zirconia ($ZrO_2$) powder having an average particle diameter of 200 nm which were mixed at a weight ratio of 0.5:0.5. A rubber-based composition used as Comparative Example 8 was prepared by silicone rubber and a barium sulfate ($BaSO_4$) powder having an average particle diameter of 30 nm which were mixed at a weight ratio of 0.5:0.5.

The evaluation rubber plates obtained in Examples 1 to 5 and Comparative Examples 1 to 8 were used to obtain the density, longitudinal wave sound velocity, acoustic impedance, attenuation ratio, and FOM value. In addition, the hollow rubber caps of these examples and comparative examples were used to obtain the molding percent defective. The results are shown in Table 1 below.

The density was obtained by measuring the weight of the evaluation rubber plate and also measuring its volume with a vernier caliper.

The attenuation ratio and sound velocity of the evaluation rubber plate were measured using a 10-MHz measurement ultrasonic probe by an underwater method. These measurements were done at a water temperature of 37° C. The FOM value (sound velocity×attenuation ratio) was obtained from the measured sound velocity and attenuation ratio.

The acoustic impedance was calculated as the product of the obtained sound velocity and density.

The lens molding properties were evaluated as a molding percent defective (%) by molding 20 hollow rubber caps and observing cracks and pores.

TABLE 1

| | Acoustic lens composition (weight ratio) | | | Acoustic lens characteristics | | | | Molding |
| --- | --- | --- | --- | --- | --- | --- | --- | --- |
| | Silicone rubber | ZnO powder (30 nm) | $SiO_2$ powder (16 nm) | Density (g/cm³) | Longitudinal wave sound velocity (m/s) | Acoustic impedance (MRayls) | Attenuation ratio (dB/mm) | Figure of merit | percent defective (%) |
| Example 1 | 0.6 | 0.4 | 0 | 1.49 | 920 | 1.370 | 7.9 | 7268 | 0 |
| Example 2 | 0.5 | 0.5 | 0 | 1.70 | 880 | 1.439 | 9.4 | 8272 | 0 |
| Example 3 | 0.45 | 0.55 | 0 | 1.82 | 860 | 1.569 | 10.8 | 9288 | 0 |
| Example 4 | 0.5 | 0.4 | 0.1 | 1.62 | 880 | 1.427 | 9.1 | 8008 | 0 |
| Example 5 | 0.48 | 0.42 | 0.1 | 1.67 | 888 | 1.479 | 9.4 | 8437 | 0 |
| Comparative Example 1 | 0.9 | 0.1 | 0 | 1.09 | 1010 | 1.100 | 3.8 | 3838 | 0 |
| Comparative Example 2 | 0.38 | 0.62 | 0 | 2.04 | 860 | 1.753 | 13.5 | 11610 | 10 |
| Comparative Example 3 | 0.5 | 0 | 0.5 | 1.38 | 1030 | 1.416 | 10.2 | 10506 | 30 |
| Comparative Example 4 | 0.45 | $TiO_2$: 0.55 | | 1.72 | 890 | 1.540 | 11.5 | 10235 | 20 |
| Comparative Example 5 | 0.45 | $Al_2O_3$: 0.55 | | 1.70 | 920 | 1.564 | 11.6 | 10672 | 15 |
| Comparative Example 6 | 0.48 | Butadiene rubber: 0.48 ZnO: 0.04 | | 1.03 | 1170 | 1.210 | 2.5 | 2925 | 60 |
| Comparative Example 7 | 0.5 | $ZrO_2$: 0.5 | | 1.70 | 880 | 1.496 | 17 | 14960 | 0 |
| Comparative Example 8 | 0.5 | $BaSO_4$: 0.5 | | 1.64 | 920 | 1.509 | 15 | 13800 | 10 |

As shown in Table 1, each of the vulcanized molded products of Examples 1 to 5 having acoustic lens compositions containing 40 wt % or more of silicone rubber and 15 to 60 wt % of a ZnO powder had an acoustic impedance of 1.370 to 1.569 MRayls which was close to the acoustic impedance (1.53 MRayls) of a living body. When an acoustic lens is formed, therefore, reverberation in a living body can be reduced. Also, each of the vulcanized molded products of Examples 1 to 5 had a longitudinal wave sound velocity of 1,000 m/s or less, an attenuation ratio of 11 dB/mm or less at a frequency of 10 MHz, and an FOM value of 9,500 or less. Accordingly, attenuation of an ultrasonic wave can be reduced when an acoustic lens is formed, so a high-sensitivity ultrasonic probe can be manufactured. In the vulcanized molded products of Examples 1 to 5, since no molding defects occurred at all when cap-like acoustic lenses were molded by using the acoustic lens compositions, the manufacturing yield was high.

By contrast, the vulcanized molded product of Comparative Example 1 having an acoustic lens composition in which silicon rubber and a ZnO powder were mixed at 0.9:0.1, i.e., the amount of ZnO powder was smaller than those of the present invention had an acoustic impedance of 1.100 MRayls which was largely different from the acoustic impedance (1.53 MRayls) of a living body. When an acoustic lens is formed, therefore, reverberation occurs in a living body.

The vulcanized molded product of Comparative Example 2 having an acoustic lens composition in which silicon rubber and a ZnO powder were mixed at 0.38:0.62, i.e., the amount of ZnO powder was larger than those of the present invention had a high attenuation ratio of 13.5 dB/mm and a large FOM value of 10,000 or more. In addition, the molding percent defective was 10%, indicating a low manufacturing yield.

The vulcanized molded product of Comparative Example 3 having an acoustic lens composition in which silicon rubber and an $SiO_2$ powder were mixed at 0.5:0.5 so that the acoustic impedance was 1.416 MRayls, i.e., close to the acoustic impedance (1.53 MRayls) of a living body had a large FOM value of 10,000 or more. Also, the molding percent defective was 30%, i.e., the manufacturing yield was very low.

The vulcanized molded product of Comparative Example 4 having an acoustic lens composition in which silicon rubber and a $TiO_2$ powder were mixed at 0.45:0.55, and the vulcanized molded product of Comparative Example 5 having a composition in which silicon rubber and an $Al_2O_3$ powder were mixed at 0.45:0.55, so that the acoustic impedance was close to the acoustic impedance (1.53 MRayls) of a living body, had large FOM values of 10,000 or more. In addition, the molding percent defectives were 20% and 15%, indicating very low manufacturing yields.

The vulcanized molded product of Comparative Example 6 having an acoustic lens composition in which silicon rubber, butadiene rubber, and a ZnO powder were mixed at 0.48:0.48:0.04 had an acoustic impedance of 1.210 MRayls which was largely different from the acoustic impedance (1.53 MRayls) of a living body, and a molding percent defective of 60%, i.e., a very low manufacturing yield. Also, this vulcanized molded product was inferior to Examples 1 to 5 in solubility in castor oil or olive oil, and hence was of no practical use as an acoustic lens.

The vulcanized molded product of Comparative Example 7 having an acoustic lens composition in which silicon rubber and a $ZrO_2$ powder equal in density to ZnO were mixed at 0.5:0.5 so that the acoustic impedance was close to the acoustic impedance (1.53 MRayls) of a living body had a high attenuation ratio of 17 dB/mm and a large FOM value of 10,000 or more.

The vulcanized molded product of Comparative Example 8 having an acoustic lens composition in which silicon rubber and a $BaSO_4$ powder equal in density to ZnO were mixed at 0.5:0.5 so that the acoustic impedance was close to the acoustic impedance (1.53 MRayls) of a living body had a high attenuation ratio of 15 dB/mm and a large FOM value of 10,000 or more. Also, the molding percent defective was 10%, indicating a low manufacturing yield.

Note that when 10-MHz acoustic lenses having a focus of 15 mm were manufactured using the acoustic lens composition containing silicone rubber and a ZnO powder in Example 1 and the acoustic lens composition containing silicone rubber and an $SiO_2$ powder in Comparative Example 3, the thickness of the acoustic lens of Example 1 was made smaller by about 15% than that of the acoustic lens of Comparative Example 3. This makes the final attenuation difference between the acoustic lenses be 4 dB/mm or more. Accordingly, a high-sensitivity ultrasonic probe can be realized by using the rubber-based composition of Example 1.

Note also that when 3-MHz, low-frequency acoustic lenses having a focus of 80 mm were manufactured, the thickness of the acoustic lens of Example 1 was made smaller by about 25% than that of the acoustic lens of Comparative Example 3. This makes the final attenuation difference between the acoustic lenses be 3 dB/mm or more. Accordingly, the performance of a 3 to 12 MHz ultrasonic probe can be improved by using the acoustic lens composition of Example 1.

EXAMPLE 6

First, a platinum (Pt) powder having an average particle diameter of 15 nm was placed in a thermostat bath at 200° C. and dried for 2 hrs to evaporate adhered water and the like.

A rubber-based composition was prepared by weighing materials such that the amount of silicone rubber as base rubber was 0.65 parts by weight and the amount of Pt powder was 0.35 parts by weight. This rubber-based composition was well kneaded by using a two-stage roll. Subsequently, 2,5-dimethyl-2,5-ditertiarybutylperoxyhexane as a vulcanizing agent was added to the rubber-based composition such that the amount of the vulcanizing agent was 1.0 wt % with respect to the silicone rubber in the rubber-based composition, and the resultant acoustic lens composition was further kneaded. After that, the kneaded acoustic lens composition underwent vulcanization molding at a temperature of 170° C. for 15 min to mold a 30×30×1 $mm^3$ square rubber plate for evaluation. In addition, the same kneaded product was used to form a hollow rubber cap 10 shown in FIG. 2 under the same conditions by vulcanization molding. These vulcanized molded products underwent secondary vulcanization for 4 hrs in a dryer held at 200° C.

EXAMPLES 7-14

Vulcanized molded products (evaluation rubber plates and hollow rubber caps) having undergone secondary vulcanization were manufactured following the same procedures as in Example 6, except that eight types of rubber-based compositions described below were used. A rubber-based composition used as Example 7 was prepared by silicone rubber and a Pt powder having an average particle diameter of 15 nm which were mixed at weight ratio of 0.55:0.45. A rubber-based composition used as Example 8 was prepared by silicone rubber and a Pt powder having an average particle diameter of 15 nm which were mixed at weight ratio of 0.48:0.52. A rubber-based composition used as Example 9 was prepared by silicone rubber, a Pt powder having an average particle diameter of 15 nm, and a silica ($SiO_2$) powder having an average particle diameter of 16 nm which were mixed at weight ratio of 0.5:0.4:0.1. A rubber-based composition used as Example 10 was prepared by silicone rubber, a Pt powder having an average particle diameter of 15 nm, and a silica ($SiO_2$) powder having an average particle diameter of 16 nm which were mixed at weight ratio of 0.5:0.3:0.2. A rubber-based composition used as Example 11 was prepared by silicone rubber, a Pt powder having an average particle diameter of 15 nm, and a silica ($SiO_2$) powder having an average particle diameter of 16 nm which were mixed at weight ratio of 0.5:0.2:0.3. A rubber-based composition used as Example 12 was prepared by silicone rubber, a Pt powder having an average particle diameter of 15 nm, and a silica ($SiO_2$) powder having an average particle diameter of 16 nm which were mixed at weight ratios of 0.55:0.15:0.3. A rubber-based composition used as Example 13 was prepared by silicone rubber and a Pt powder having an average particle diameter of 50 nm which were mixed S at a weight ratio of 0.65:0.35. A rubber-based composition used as Example 14 was prepared by silicone rubber and a Pt powder having an average particle diameter of 200 nm which were mixed at a weight ratio of 0.65:0.35.

COMPARATIVE EXAMPLES 9 & 10

Vulcanized molded products (evaluation rubber plates and hollow rubber caps) having undergone secondary vulcanization were manufactured following the same procedures as in Example 6, except that two types of rubber-based compositions described below were used. A rubber-based composition used as Comparative Examples 9 was prepared by silicone rubber and a Pt powder having an average particle diameter of 15 nm which were mixed at a weight ratio of 0.92:0.08. A rubber-based composition used as Comparative Examples 10 was prepared by silicone rubber and a Pt powder having an average particle diameter of 15 nm which were mixed at a weight ratio of 0.4:0.6.

COMPARATIVE EXAMPLE 11

Vulcanized molded products (evaluation rubber plates and hollow rubber caps) having undergone secondary vulcanization were manufactured following the same procedures as in Example 6, except that a rubber-based composition in which silicone rubber and a gold (Au) powder having an average particle diameter of 200 nm were mixed at a weight ratio of 0.5:0.5 was used.

The evaluation rubber plates obtained in Examples 6 to 14 and Comparative Examples 9 to 11 were used to obtain the density, longitudinal wave sound velocity, acoustic impedance, attenuation ratio, and FOM value following the same procedures as in Example 1. In addition, the hollow rubber caps of these examples 6 to 14 and comparative examples 9 to 11 were used to obtain the molding percent defective in the same manner as in Example 1. The results are shown in Table 2 below.

TABLE 2

| | Acoustic lens composition (weight ratio) | | | Acoustic lens characteristics | | | | Molding |
|---|---|---|---|---|---|---|---|---|
| | Silicone rubber | ZnO powder (15 nm) | $SiO_2$ powder (16 nm) | Density (g/cm³) | Longitudinal wave sound velocity (m/s) | Acoustic impedance (MRayls) | Attenuation ratio (dB/mm) | Figure of merit | percent defective (%) |
| Example 6 | 0.65 | 0.35 | 0 | 1.50 | 920 | 1.381 | 8.2 | 7544 | 0 |
| Example 7 | 0.55 | 0.45 | 0 | 1.75 | 860 | 1.506 | 10.5 | 9030 | 0 |
| Example 8 | 0.48 | 0.52 | 0 | 1.98 | 820 | 1.626 | 11.4 | 9348 | 0 |
| Example 9 | 0.5 | 0.4 | 0.1 | 1.77 | 880 | 1.560 | 11.0 | 9680 | 0 |
| Example 10 | 0.5 | 0.3 | 0.2 | 1.65 | 900 | 1.488 | 10.8 | 9720 | 0 |
| Example 11 | 0.5 | 0.2 | 0.3 | 1.55 | 920 | 1.425 | 10.5 | 9660 | 5 |
| Example 12 | 0.55 | 0.15 | 0.3 | 1.44 | 980 | 1.413 | 9.2 | 9016 | 5 |
| Example 13 | 0.65 | 0.35 (50 nm) | 0 | 1.50 | 910 | 1.365 | 8.8 | 8008 | 0 |
| Example 14 | 0.65 | 0.35 (200 nm) | 0 | 1.50 | 900 | 1.350 | 9.1 | 8190 | 0 |
| Comparative Example 9 | 0.92 | 0.08 | 0 | 1.08 | 990 | 1.072 | 3.6 | 3564 | 0 |
| Comparative Example 10 | 0.4 | 0.6 | 0 | 2.34 | 800 | 1.869 | 16.0 | 12800 | 5 |
| Comparative Example 11 | 0.5 | Au: 0.5 | | 1.74 | 850 | 1.479 | 25.0 | 21250 | 0 |

As shown in Table 2, each of the vulcanized molded products of Examples 6 to 14 having acoustic lens compositions containing 40 wt % or more of silicone rubber and 10 to 52 wt % of a Pt powder had an acoustic impedance of 1.350 to 1.626 MRayls which was close to the acoustic impedance (1.53 MRayls) of a living body. When an acoustic lens is formed, therefore, reverberation in a living body can be reduced. Also, each of the vulcanized molded products of Examples 6 to 14 had a longitudinal wave sound velocity of 1,000 m/s or less, an attenuation ratio of 11.4 dB/mm or less at a frequency of 10 MHz, and a small FOM value of 9,700 or less. Accordingly, attenuation of an ultra sonic can be reduced when an acoustic lens is formed, so a high-sensitivity ultrasonic probe can be manufactured. In the vulcanized molded products of Examples 6 to 10, 13, and 14, since no molding defects occurred at all when cap-like acoustic lenses were molded by using the acoustic lens compositions, the manufacturing yield was high. When the vulcanized molded products of examples 11 and 12 in which 30 wt % of an $SiO_2$ powder were mixed were used, the molding percent defective was 5%, i.e., the manufacturing yield slightly lowered. However, the total acoustic lens characteristics were excellent.

In the vulcanized molded products of Examples 6, 13, and 14 having the same composition but using Pt powders different in average particle diameter, as the average particle diameter increased, the sound velocity slightly decreased, and the FOM value increased, although the density remained unchanged. That is, the FOM value can be decreased by decreasing the particle diameter of a Pt powder.

By contrast, the vulcanized molded product of Comparative Example 9 having an acoustic lens composition in which silicon rubber and a Pt powder were mixed at 0.92:0.08, i.e., the amount of Pt powder was smaller than those of the present invention had an acoustic impedance of 1.072 MRayls which was largely different from the acoustic impedance (1.53

MRayls) of a living body. When an acoustic lens is formed, therefore, reverberation occurs in a living body.

The vulcanized molded product of Comparative Example 10 having an acoustic lens composition in which silicon rubber and a Pt powder were mixed at 0.4:0.6, i.e., the amount of Pt powder was larger than those of the present invention had a large attenuation ratio of 16.0 dB/mm and a large FOM value of 10,000 or more. In addition, the molding percent defective was 5%, i.e., the manufacturing yield also slightly lowered.

The vulcanized molded product of Comparative Example 11 having an acoustic lens composition in which silicon rubber and an Au powder equal in density to Pt were mixed at 0.5:0.5 so that the acoustic impedance was close to the acoustic impedance (1.53 MRayls) of a living body had a high attenuation ratio of 25 dB/mm and a large FOM value of 10,000 or more.

EXAMPLE 15

First, a ytterbium oxide ($Yb_2O_3$) powder having an average particle diameter of 25 nm was placed in a thermostat bath at 200° C. and dried for 2 hrs to evaporate adhered water and the like.

A rubber-based composition was prepared by weighing materials such that the amount of silicone rubber as base rubber was 0.65 parts by weight and the amount of ytterbium oxide powder was 0.35 parts by weight. This rubber-based composition was well kneaded by using a two-stage roll. Subsequently, 2,5-dimethyl-2,5-ditertiarybutylperoxyhexane as a vulcanizing agent was added to the rubber-based composition such that the amount of the vulcanizing agent was 1.0 wt % with respect to the silicone rubber in the rubber-based composition, and the resultant acoustic lens composition was further kneaded. After that, the kneaded acoustic lens composition underwent vulcanization molding at a temperature of 170° C. for 15 min to mold a 30×30×1 mm³ square rubber plate for evaluation. In addition, the same kneaded product was used to form a hollow rubber cap 10 shown in FIG. 2 under the same conditions by vulcanization molding. These vulcanized molded products underwent secondary vulcanization for 4 hrs in a dryer held at 200° C.

EXAMPLES 16-22

Vulcanized molded products (evaluation rubber plates and hollow rubber caps) having undergone secondary vulcanization were manufactured following the same procedures as in Example 15, except that seven types of rubber-based compositions described below were used. A rubber-based composition used as Example 16 was prepared by silicone rubber and a $Yb_2O_3$ powder having an average particle diameter of 25 nm which were mixed at weight ratio of 0.6:0.4. A rubber-based composition used as Example 17 was prepared by silicone rubber and a $Yb_2O_3$ powder having an average particle diameter of 25 nm which were mixed at weight ratio of 0.45:0.55. A rubber-based composition used as Example 18 was prepared by silicone rubber, a $Yb_2O_3$ powder having an average particle diameter of 25 nm, and a silica ($SiO_2$) powder having an average particle diameter of 19 nm which were mixed at weight ratio of 0.55:0.4:0.05. A rubber-based composition used as Example 19 was prepared by silicone rubber, a $Yb_2O_3$ powder having an average particle diameter of 25 nm, and a silica ($SiO_2$) powder having an average particle diameter of 16 nm which were mixed at weight ratio of 0.5:0.4:0.1. A rubber-based composition used as Example 20 was prepared by silicone rubber, a $Yb_2O_3$ powder having an average particle diameter of 25 nm, and a silica ($SiO_2$) powder having an average particle diameter of 16 nm which were mixed at weight ratio of 0.5:0.3:0.2. A rubber-based composition used as Example 21 was prepared by silicone rubber, a $Yb_2O_3$ powder having an average particle diameter of 25 nm, and a silica ($SiO_2$) powder having an average particle diameter of 16 nm which were mixed at weight ratio of 0.5:0.2:0.3. A rubber-based composition used as Example 22 was prepared by silicone rubber, a silicone-resin-coated $Yb_2O_3$ powder having an average particle diameter of 25 nm, and a silica ($SiO_2$) powder having an average particle size of 16 nm which were mixed at a weight ratio of 0.5:0.4:0.1.

COMPARATIVE EXAMPLES 12 & 13

Vulcanized molded products (evaluation rubber plates and hollow rubber caps) having undergone secondary vulcanization were manufactured following the same procedures as in Example 15, except that two types of rubber-based compositions described below were used. A rubber-based composition used as Comparative Example 12 was prepared by silicone rubber and a $Yb_2O_3$ powder having an average particle diameter of 25 nm which were mixed at a weight ratio of 0.92:0.08. A rubber-based composition used as Comparative Example 13 was prepared by silicone rubber and a $Yb_2O_3$ powder having an average particle diameter of 25 nm which were mixed at a weight ratio of 0.35:0.65.

COMPARATIVE EXAMPLES 14 & 15

Vulcanized molded products (evaluation rubber plates and hollow rubber caps) having undergone secondary vulcanization were manufactured following the same procedures as in Example 15, except that two types of rubber-based compositions described below were used. A rubber-based composition used as Comparative Example 14 was prepared by silicone rubber and a lutetium oxide ($Lu_2O_3$) powder having an average particle diameter of 25 nm which were mixed at a weight ratio of 0.55:0.45. A rubber-based composition used as Comparative Example 15 was prepared by silicone rubber and a bismuth oxide ($Bi_2O_3$) powder having an average particle diameter of 300 nm which were mixed at a weight ratio of 0.55:0.45.

The evaluation rubber plates obtained in Examples 15 to 22 and Comparative Examples 12 to 15 were used to obtain the density, longitudinal wave sound velocity, acoustic impedance, attenuation ratio, and FOM value following the same procedures as in Example 1. In addition, the hollow rubber caps of these examples 15 to 22 and comparative examples 12 to 15 were used to obtain the molding percent defective in the same manner as in Example 1. The results are shown in Table 3 below.

TABLE 3

| | Acoustic lens composition (weight ratio) | | | Acoustic lens characteristics | | | | | Molding |
|---|---|---|---|---|---|---|---|---|---|
| | Silicone rubber | Yb$_2$O$_3$ powder (25 nm) | SiO$_2$ powder (16 nm) | Density (g/cm$^3$) | Longitudinal wave sound velocity (m/s) | Acoustic impedance (MRayls) | Attenuation ratio (dB/mm) | Figure of merit | percent defective (%) |
| Example 15 | 0.65 | 0.35 | 0 | 1.45 | 943 | 1.371 | 7.8 | 7355 | 0 |
| Example 16 | 0.6 | 0.4 | 0 | 1.55 | 895 | 1.391 | 8.2 | 7339 | 0 |
| Example 17 | 0.45 | 0.55 | 0 | 1.96 | 840 | 1.648 | 11.4 | 9576 | 0 |
| Example 18 | 0.55 | 0.4 | 0.05 | 1.62 | 895 | 1.452 | 9.0 | 8055 | 0 |
| Example 19 | 0.5 | 0.4 | 0.1 | 1.70 | 880 | 1.494 | 10.1 | 8888 | 0 |
| Example 20 | 0.5 | 0.3 | 0.2 | 1.60 | 900 | 1.443 | 9.5 | 8550 | 0 |
| Example 21 | 0.5 | 0.2 | 0.3 | 1.53 | 940 | 1.482 | 10.0 | 9400 | 0 |
| Example 22 | 0.5 | 0.4 (Si coat) | 0.1 | 1.70 | 880 | 1.494 | 9.5 | 8360 | 0 |
| Comparative Example 12 | 0.92 | 0.08 | 0 | 1.08 | 1000 | 1.077 | 4.0 | 4000 | 0 |
| Comparative Example 13 | 0.35 | 0.65 | 0 | 2.38 | 820 | 1.949 | 14.5 | 11890 | 10 |
| Comparative Example 14 | 0.55 | Lu$_2$O$_3$: 0.5 | | 1.67 | 900 | 1.503 | 12.0 | 10800 | 0 |
| Comparative Example 15 | 0.5 | Bi$_2$O$_3$: 0.5 | | 1.80 | 850 | 1.530 | 14.0 | 11900 | 0 |

As shown in Table 3, each of the vulcanized molded products of Examples 15 to 22 having acoustic lens compositions containing 40 wt % or more of silicone rubber and 12 to 56 wt % of a Yb$_2$O$_3$ powder had an acoustic impedance of 1.371 to 1.648 MRayls which was close to the acoustic impedance (1.53 MRayls) of a living body. When an acoustic lens is formed, therefore, reverberation in a living body can be reduced. Also, each of the vulcanized molded products of Examples 15 to 22 had a longitudinal wave sound velocity of 1,000 m/s or less, an attenuation ratio of 11.4 dB/mm or less at a frequency of 10 MHz, and a small FOM value of 9,600 or less. Accordingly, attenuation of an ultra sonic can be reduced when an acoustic lens is formed, so a high-sensitivity ultrasonic probe can be manufactured. In particular, the vulcanized molded product of Example 22 using the Yb$_2$O$_3$ powder whose surface was coated with a silicone resin had the same density and sound velocity as those of the vulcanized molded product of Example 19 having the same composition, but had a lower attenuation ratio and smaller FOM value. Furthermore, in the vulcanized molded products of Examples 15 to 22, no molding defects occurred at all when cap-like acoustic lenses were molded by using the acoustic lens compositions, so the manufacturing yield was also high.

By contrast, the vulcanized molded product of Comparative Example 12 having an acoustic lens composition in which silicon rubber and a Yb$_2$O$_3$ powder were mixed at 0.92:0.08, i.e., the amount of Yb$_2$O$_3$ powder was smaller than those of the present invention had an acoustic impedance of 1.077 MRayls which was largely different from the acoustic impedance (1.53 MRayls) of a living body. When an acoustic lens is formed, therefore, reverberation occurs in a living body.

The vulcanized molded product of Comparative Example 13 having an acoustic lens composition in which silicon rubber and a Yb$_2$O$_3$ powder were mixed at 0.35:0.65, i.e., the amount of Yb$_2$O$_3$ powder was larger than those of the present invention had a high attenuation ratio of 14.5 dB/mm and a large FOM value of 10,000 or more. In addition, the molding percent defective was 10%, i.e., the manufacturing yield also lowered.

The vulcanized molded products of Comparative Examples 14 and 15 having acoustic lens compositions in which silicon rubber and powders of Lu$_2$O$_3$ and Bi$_2$O$_3$ equal in density to Yb$_2$O$_3$ were mixed at 0.55:0.45 and 0.5:0.5, respectively, so that the acoustic impedances were close to the acoustic impedance (1.53 MRayls) of a living body had high attenuation ratios of 12 and 14 dB/mm, respectively, and large FOM values of 10,000 or more.

EXAMPLE 23

First, a zinc oxide (ZnO) powder having an average particle diameter of 30 nm, a platinum (Pt) powder having an average particle diameter of 15 nm, and a ytterbium oxide (Yb$_2$O$_3$) powder having an average particle diameter of 25 nm were placed in a high-temperature bath at 200° C. and dried for 2 hrs to evaporate adhered water and the like.

A rubber-based composition was prepared by weighing materials such that the amount of silicone rubber as base rubber was 50 wt % and the amounts of ZnO powder, Pt powder, Yb$_2$O$_3$ powder, and SiO$_2$ powder were 15, 15, 15, and 5 wt %, respectively. This rubber-based composition was well kneaded by using a two-stage roll. Subsequently, 2,5-dimethyl-2,5-ditertiarybutylperoxyhexane as a vulcanizing agent was added to the rubber-based composition such that the amount of the vulcanizing agent was 1.0 wt % with respect to the silicone rubber in the rubber-based composition, and the resultant acoustic lens composition was further kneaded. After that, the kneaded acoustic lens composition underwent vulcanization molding at a temperature of 170° C. for 15 min to mold a 30×30×1 mm$^3$ square rubber plate for evaluation. In addition, the same kneaded product was used to form a hollow rubber cap 10 shown in FIG. 2 under the same conditions by vulcanization molding. These vulcanized molded products underwent secondary vulcanization for 4 hrs in a dryer held at 200° C.

The evaluation rubber plate obtained in Example 23 was used to obtain the density, longitudinal wave sound velocity, acoustic impedance, attenuation ratio, and FOM value following the same procedures as in Example 1. In addition, the hollow rubber cap was used to obtain the molding percent defective in the same manner as in Example 1.

Consequently, the density was 1.75 g/cm$^3$, the longitudinal wave sound velocity was 890 m/s, the acoustic impedance was 1.554 Mrayls, the attenuation ratio was 10.2 dB/mm, and the FOM value was 9,078. When an acoustic lens is formed, therefore, reverberation in a living body can be reduced, so attenuation can be reduced. Accordingly, a high-sensitivity ultrasonic probe can be manufactured. Also, the molding percent defective was 0%, indicating a high manufacturing yield.

FIG. 3 shows the relationship between the acoustic impedance and the FOM value at 10 MHz of each of the vulcanized molded products of Examples 1 to 23 described above. It is clearly understood from FIG. 3 that each of the vulcanized molded products of Examples 1 to 23 had an acoustic impedance close to that of a living body and a small FOM value as the product of the sound velocity and attenuation ratio, i.e., each vulcanized molded product was superior in total characteristics required of an acoustic lens.

Additional advantages and modifications will readily occur to those skilled in the art. Therefore, the invention in its broader aspects is not limited to the specific details and representative embodiments shown and described herein. Accordingly, various modifications may be made without departing from the spirit and scope of the general inventive concept as defined by the appended claims and their equivalents.

What is claimed is:

1. An ultrasonic probe comprising:
   a backing material;
   a piezoelectric element formed on the backing material, and having a piezoelectric body and a pair of electrodes formed on a first surface of the piezoelectric body, which faces the backing material, and on a second surface of the piezoelectric body, which is opposite to the first surface;
   an acoustic matching layer formed on the piezoelectric element; and
   an acoustic lens formed on the acoustic matching layer and comprising not less than 40 wt % of silicone rubber, 15 to 60 wt % of a zinc oxide powder having an average particle diameter of 10 to 50 nm and a density of about 5.6 g/cm$^3$, and not more than 30 wt % of a silica powder, and having a sound velocity of about 820 to 980 m/s and an acoustic impedance of about 1.3 to 1.7 MRayls.

2. A probe according to claim 1, wherein the silicon rubber in the acoustic lens is liquid silicone rubber.

3. A probe according to claim 1, wherein the silicone rubber in the acoustic lens is millable silicone rubber.

4. A probe according to claim 1, wherein a surface of the zinc oxide powder in the acoustic lens is coated with a silicone resin.

5. An ultrasonic diagnostic apparatus comprising:
   an ultrasonic probe comprising a piezoelectric element, an acoustic matching layer formed on the piezoelectric element and an acoustic lens formed on the acoustic matching layer, and the acoustic lens comprising not less than 40 wt % of silicone rubber, 15 to 60 wt % of a zinc oxide powder having an average particle diameter of 10 to 50 nm and a density of about 5.6 g/cm$^3$, and not more than 30 wt % of a silica powder, and having a sound velocity of about 820 to 980 m/s and an acoustic impedance of about 1.3 to 1.7 MRayls;
   an ultrasonic diagnostic apparatus main body having a screen; and
   a cable which connects the ultrasonic probe and ultrasonic diagnostic apparatus main body.

* * * * *